United States Patent [19]

Petersen et al.

[11] 4,438,260
[45] Mar. 20, 1984

[54] SISOMICIN COMPOUNDS

[75] Inventors: Uwe Petersen, Leverkusen; Peter Stadler, Haan; Oswald Lockhoff, Leverkusen; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 334,401

[22] Filed: Dec. 24, 1981

[30] Foreign Application Priority Data

Jan. 17, 1981 [DE] Fed. Rep. of Germany ....... 3101376

[51] Int. Cl.$^3$ .............................................. C07H 15/22
[52] U.S. Cl. .................................. 536/13.9; 424/180; 536/16.8

[58] Field of Search ...................... 536/13.9; 424/180

[56] References Cited

U.S. PATENT DOCUMENTS 4,234,572 11/1980 Petersen et al. .................. 536/13.9
4,312,859 1/1982 Petersen et al. .................. 536/13.9

Primary Examiner—Johnnie R. Brown
Assistant Examiner—Elli Peseler
Attorney, Agent, or Firm—Sprung, Horn, Kramer & Woods

[57] ABSTRACT

The invention relates to sisomicin derivatives of formula (I) and methods for their preparation. Also included in the invention are compositions containing said sisomicin derivatives and the use of said derivatives and compositions for the treatment of bacterial infections.

2 Claims, No Drawings

SISOMICIN COMPOUNDS

The present invention relates to certain new sisomicin derivatives, to a process for their production and to their use as medicaments.

Sisomicin is an antibacterial compound from the group comprising the aminoglycoside antibiotics. Aminoglycoside antibiotics have attained great importance in combating bacterial infections. However, the appearance of resistant germs reduces their wide applicability in many cases; furthermore, side-effects such as ototoxicity and nephrotoxicity can occur. These disadvantages can be eliminated in some cases by preparing derivatives.

Thus, for example, 1-N-(aminoalkyloxycarbonyl)-sisomicin derivatives which are distinguished by a high activity against sisomicin-resistant germs have been disclosed in German Published Specification No. 2,753,769 corresponding to U.S. Ser. No. 960,205, now U.S. Pat. No. 4,234,572 issued Nov. 18, 1980.

In an unobvious development of the technical teaching of DE-OS (German Published Specification) No. 2,753,769, the compounds according to the invention, which are antibiotically particularly active, have now been found.

According to the present invention there are provided compounds which are sisomicin derivatives of the formula

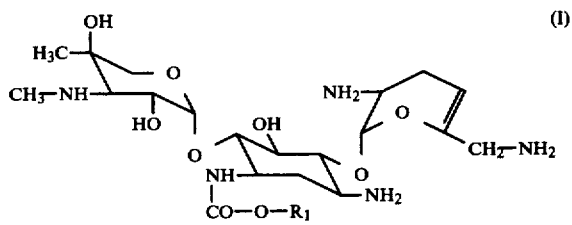

or a salt thereof, wherein $R_1$ denotes a radical of the general formula —A—XH, in which A represents an optionally branched alkylene or alkenylene radical which has 3 to 7, preferably 4 to 6 carbon atoms and which is substituted by 2 to 4 hydroxyl groups, and X represents oxygen or, preferably, a group of the general formula —$NR_2$—, in which $R_2$ represents a hydrogen atom, an alkyl or hydroxyalkyl group having 1 to 6, preferably 2 to 4, carbon atoms, or an aralkyl group having 7 to 10 carbon atoms (especially a mono- or bi-cyclic carbocyclic aryl —$C_1$—$C_2$—alkyl group), preferably a benzyl radical.

The compounds according to the invention are distinguished in comparison to the hitherto known 1-N-(aminoalkyloxycarbonyl)-sisomicin derivatives by a substantially improved tolerance, without the high antibiotic activity being restricted. The new compounds thus represent an enrichment of pharmacy.

Among the new sisomicin derivative salts of the invention, those salts that are pharmaceutically acceptable said addition salts are particularly important and are preferred.

The new free sisomicin derivatives of the formula (I) and their salts can be interconverted in any suitable manner; methods for such interconversion are known in the art.

The pharmaceutically useful salts are derived, in particular, from inorganic or organic acids (such as sulphuric acid, phosphoric acid, nitric acid, hydrochloric acid, hydrobromic acid, acetic acid, propionic acid, ascorbic acid and citric acid).

Straight-chain or branched polyhydroxyalkyl radicals and polyhydroxyalkylamino radicals, such as 2,3,4-trihydroxybutyl, 4-amino-2,3-dihydroxybutyl, 4-benzylamino-2,3-dihydroxybutyl, 4-(2,3-dihydroxypropylamino)-2,3-dihydroxybutyl, 4-dimethylamino-2,3-dihydroxybutyl, 3-amino-2,4-dihydroxybutyl, 2-amino-3,4-dihydroxybutyl, 2,3,4,5-tetrahydroxypentyl, 5-amino-2,3,4-trihydroxypentyl, 5-amino-2,3-dihydroxypentyl, 2,3,4,5,6-pentahydroxyhexyl, 6-amino-2,3,4,5-tetrahydroxyhexyl, 6-amino-4,5-dihydroxyhexyl, 1,4-dihydroxy-3-amino-but-2-yl, 1,4-dihydroxy-3-methylamio-but-2-yl, 1,4-dihydroxy-3-propylamino-but-2-yl, 1,4-dihydroxy-3-butyl-amino-but-2-yl, 1,4-dihydroxy-3-benzylamino-but-2-yl, 1,4-dihydroxy-3-(2-hydroxyethylamino)-but-2-yl, 2-amino-3-hydroxy-2-hydroxymethyl-propyl, 3-amino-2,2-bis-(hydroxymethyl)-propyl and 4-amino-2,3-bis-(hydroxymethyl)-butyl, are examples of suitable radicals $R_1$.

Particularly preferred radicals $R_1$ are those of the formulae

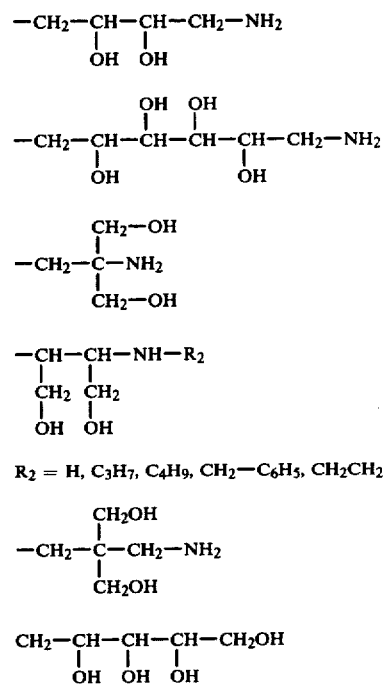

The radicals listed above are to be understood as being merely exemplary. They contain, as a rule, chiral C atoms, and are present as optically pure diastereomers or diastereomer mixtures. It can be advantageous to use the compounds according to the invention as optically pure products.

According to the present invention there is further provided a process for the production of a compound of the present invention in which a compound of the formula

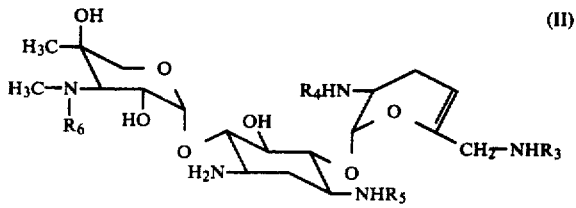

wherein $R_3$, $R_4$ and $R_5$ represent —CO—$R_7$ or —S—$R_8$, and $R_6$ represents —S—$R_8$, in which $R_7$ denotes a radical of the formulae —CHal$_3$, —(CH$_2$)$_{n_1}$—B, —O—E,

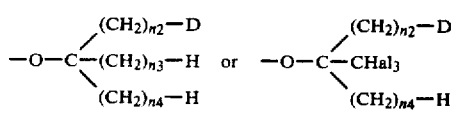

B and D denote a hydrogen atom or an optionally substituted phenyl radical,

E denotes an optionally substituted phenyl radical, $n_1$, $n_2$, $n_3$ and $n_4$ are, independently, 0, 1, 2, 3, 4 or 5, Hal denotes a fluorine, chlorine or bromine atom, and $R_8$ denotes an optionally substituted phenyl, diphenylmethyl or triphenylmethyl radical, is reacted with an acylating agent of the formula

G-CO-O-R'     (III)

wherein

G represents a leaving group (preferably a halogen atom, such as a chlorine or bromine atom or an azido or optionally substituted phenoxy radical, or a radical of the formula

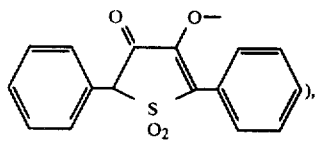

and

R' represents a radical $R_1$, as defined above, in which amino groups, if present, are protected by amino-protective groups (such as —CO—$R_7$ or —S—$R_8$), and hydroxyl groups are protected by hydroxyl-protective groups (such as the trityl group or the tetrahydropyranyl radical) or by alkylidene groups (such as isopropylidene, isobutylidene, cyclohexylidene or benzylidene), which simultaneously block two hydroxyl groups, and the protective groups $R_3$, $R_4$, $R_5$ and $R_6$, and, if appropriate, tetrahydropyranyl radicals or alkylidene groups are then split off, and the resulting compound is converted, if desired, into a salt thereof.

Preferred optionally substituted phenoxy groups of radical G are 4-nitrophenoxy, phenoxy and 2,4,5-trichlorophenoxy.

1 to 3 substituents selected from trifluoromethyl, nitro, $C_1$ to $C_4$ alkyl, $C_1$ to $C_4$ alkoxy, ($C_1$ to $C_4$ alkoxy)-carbonyl and phenyl, or 1 to 5 halogen atoms (preferably chlorine atoms) are, for example, suitable substituents of the optionally substituted phenyl, diphenylmethyl or triphenylmethyl radicals of $R_8$. o-Nitrophenylsulphenyl and 2,3,5-trichlorophenylsulphenyl may be mentioned as examples of —S$R_8$ groups.

1 or 2 substituents selected from nitro, halogen (preferably chlorine), $C_1$ to $C_4$ alkyl, $C_1$ to $C_4$ alkoxy and phenyl are suitable substituents of the optionally substituted phenyl radicals of B, D and E.

The following compounds are preferably used as starting materials of the formula (II): 2',3,3'',6'-tetra-N-(o-nitrophenylsulphenyl)-sisomicin, 3''-N-(o-nitrophenylsulphenyl)-2',3,6'-tris-N-trichloroacetyl-sisomicin, 3''-N-(o-nitrophenylsulphenyl)-2',3,6'-tris-N-trifluoroacetyl-sisomicin, 3''-N-(o-nitrophenylsulphenyl)-2',3,6'-tris-N-(2,2,2-trichloroethoxycarbonyl)-sisomicin, 3''-N-(o-nitrophenylsulphenyl)-2',3,6'-tris-N-(1,1-dimethyl-2,2,2-trichloroethoxycarbonyl)-sisomicin, 3''-N-(o-nitrophenylsulphenyl)-2',3,6'-tris-N-(4-methoxybenzyloxycarbonyl)-sisomicin, 3''-N-(o-nitrophenylsulphenyl)-2',3,6'-tris-N-phenoxycarbonylsisomicin and 3''-N-(o-nitrophenylsulphenyl)-2',3,6'-tris-N-(tert.-butoxycarbonyl)-sisomicin. The preparation of these starting materials is effected according to the processes described in DE-OS (German Published Specification) No. 2,726,197 corresponding to U.S. Ser. No. 913,135, now U.S. Pat. No. 4,190,722, issued Feb. 26, 1980 or DE-OS (German Published Specification) No. 2,840,907 corresponding to U.S. Ser. No. 74,047 now U.S. Pat. No. 4,294,959, issued Oct. 13, 1981:

The compounds of the formula (III) which are used as acylating agents can be prepared by various processes which are in themselves known, using a suitable protective group technique:

(a) The hydroxyl groups in a polyhydroxyalkyldicarboxylic acid ester such as diethyl mucate (1) (J. Org. Chem. 18, 952 [1953]) in equation (a), are reversibly blocked by reaction with an acetalising reagent, and the ester groupings are then reduced to free primary hydroxyl groups, using a reducing agent, such as lithium aluminum hydride.

One of the free hydroxyl groups is converted, using a sulphonic acid chloride in pyridine, into the sulphonic acid ester, which can be converted into an azide by a nucleophilic substitution reaction. The subsequent reduction yields an amino compound (for example the compound indicated as "(5)" in the equations which follow), which is converted into a reactive carbonate, after blocking the amino function with a protective group.

In following Equation (a), a reaction sequence is presented by way of example for diethyl mucate (the compound "(1)"), which leads to the activated carbonate (the compound "(6)"). It can also be carried out in an analogous manner using other saccharic acid esters, bishydroxymethylmalonic acid esters, and L—, D—, DL and mesotartaric acid esters. It is also indicated in Equation (a) that a substituted benzylamine is obtained, for example, by reaction of the sulphonic acid ester (the compound "(6)") with benzylamine, or by a reductive alkylation of the amine (the compound "(5)") with benzaldehyde, the substituted benzylamine yielding the activated carbonate (the compound "(7)") after reaction with 2-nitrophenylsulphenyl chloride and 4-nitrophenyl chlorocarbonate. Other amines or aldehydes can also be employed, instead of benzylamine or benzaldehyde, for this substitution reaction.

(Comment:

The following abbreviations are used in the structural formulae below and in the structural formulae in the Examples:
NPS: 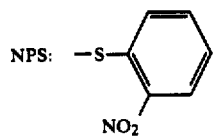   NP: 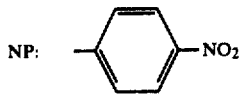
Tos: 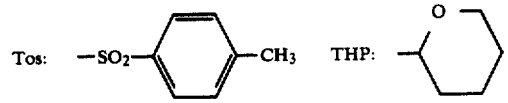   THP: 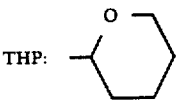
2-MBT: 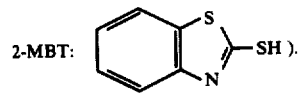
Equation (a):
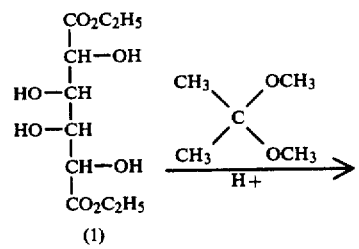
(1)
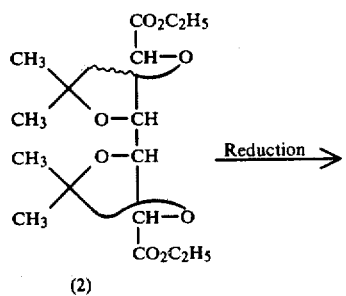
(2)
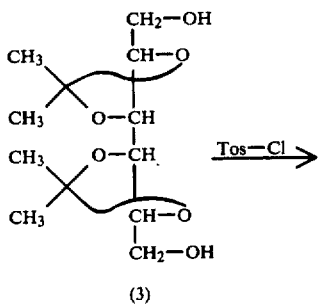
(3)

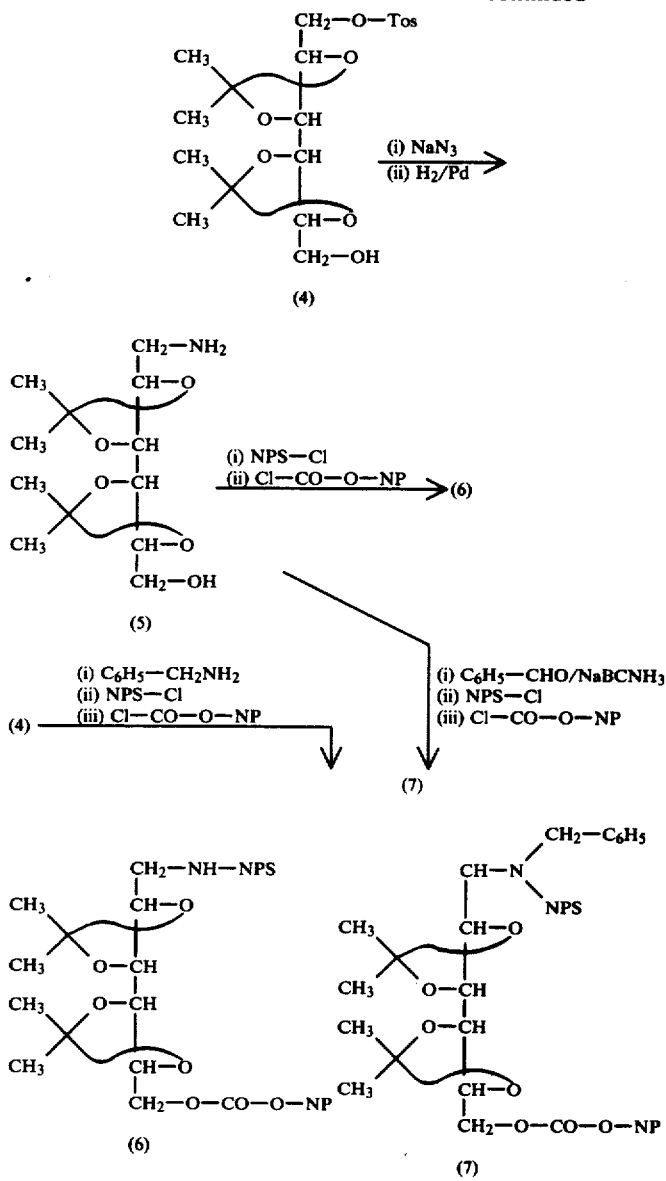

(b) By reaction of a polyhydroxyepoxide, the hydroxyl groups of which are reversibly blocked, with ammonia or an amino compound, a hydroxyamino compound is obtained, which, after the introduction of a protective group for amino and conversion of the free hydroxyl group into a reactive carbonate, is reacted to give the desired acylating agent (III).

In Equation (b) a reaction sequence using 4,4-dimethyl-3,5,8-trioxabicyclo[5.1.0]octane (the compound "(8)") (J. Org. Chem. 41, 2471 [1976]) as the starting compound is presented by way of example.

Equation (b):

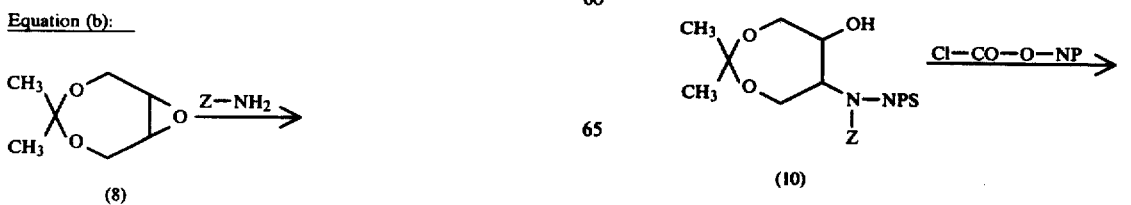

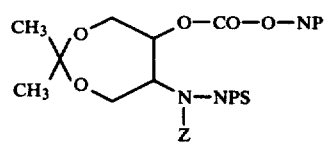
(11)

(c) In a polyhydroxyamino compound, the amino group is acylated, and all but one of the hydroxyl groups are then reversibly blocked. After the N-acyl protective group has been exchanged for a N-(2-nitrophenylsulphenyl) protective group, the free hydroxyl group is converted into a reactive carbonate.

Equation (c) shows the reactions, by way of example, using 2-amino-2-hydroxymethyl-1,3-propanediol as the starting compound.

Equation (c):

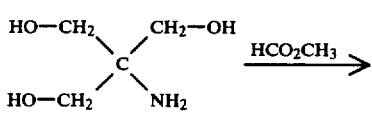

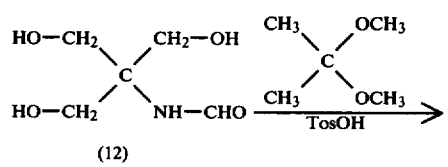
(12)

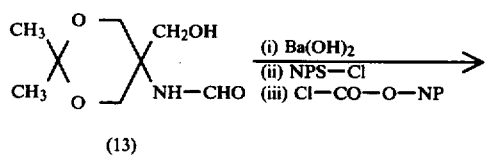
(13)

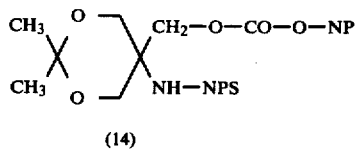
(14)

(d) All but one of the hydroxyl groups in polyhydroxy compounds are reversibly blocked by acetalisation, and the remaining free hydroxyl group is reacted to give a reactive carbonate.

In Equation (d) the reaction of 2,3,-4,5-dibenzylidenexylitol (the compound "(15)") with 4,6-diphenylthieno-[3,4-d][1,3]dioxol-2-on-5,5-dioxide (the compound "(16)") (Angew. Chem. 88 480 [1976]) to give the activated carbonate (the compound "(17)") is presented by way of example.

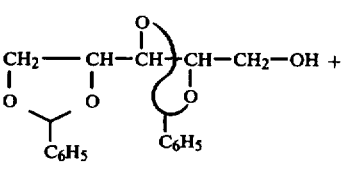
(15)

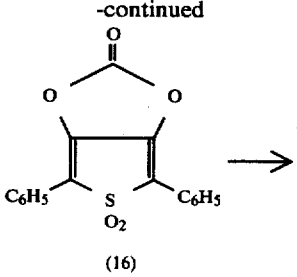
(16)

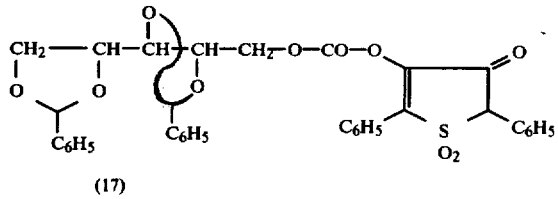
(17)

In addition to the compounds "(6)", "(7)", "(11)", "(14)" and "(17)" mentioned in Equations (a) to (d), the following compounds are examples of further suitable acylating agents of formula (III):

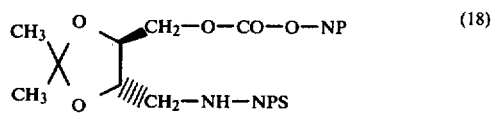
(18)

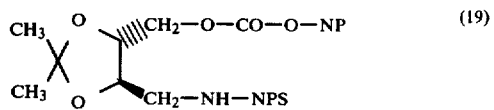
(19)

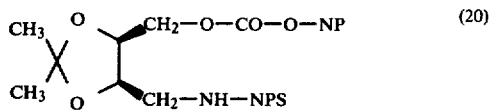
(20)

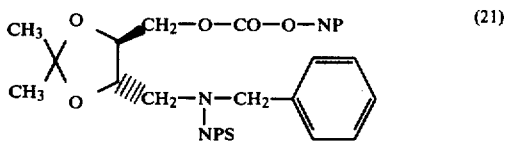
(21)

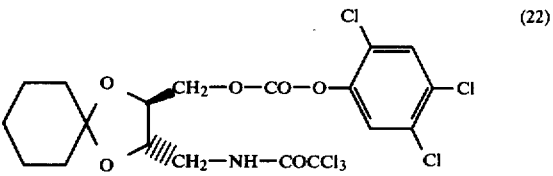
(22)

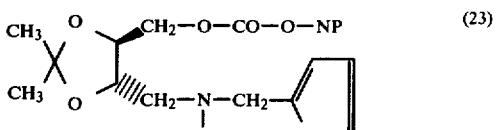
(23)

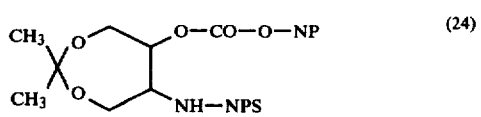
(24)

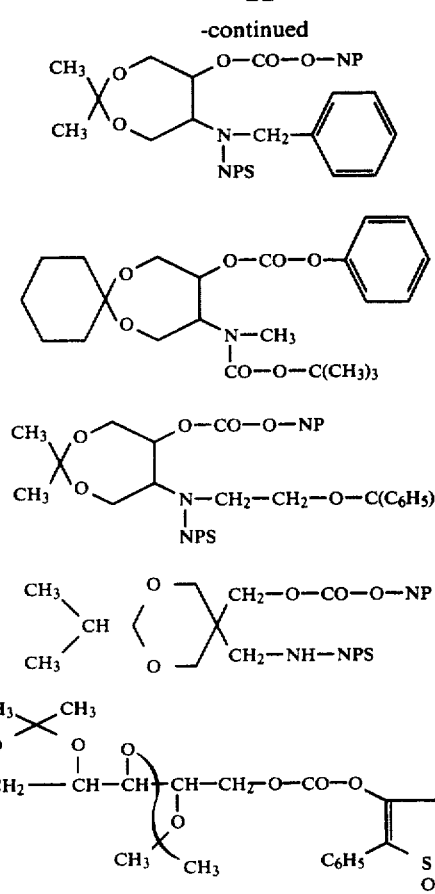

In the preparation of the compounds according to the invention, 1 mol of the compound of the formula (II) is generally reacted with 1 to 3 mol, preferably 1.1 to 1.5 mol, of a compound of the formula (III).

Any of the inert organic solvents, such as toluene, chloroform, methylene chloride, dimethylformamide, dimethylacetamide, dimethylsulphoxide, ethers (such as diethyl ether, dioxane and tetrahydrofuran), pyridine, and alcohols (such as methanol and ethanol) and mixtures thereof, are suitable diluents.

If acid-binding agents are necessary, any of the customary organic and inorganic acid-binding agents can be used. These preferably include alkali metal hydroxides and alkaline earth metal hydroxides (such as sodium hydroxide, potassium hydroxide or calcium hydroxide), alkali metal carbonates, alkaline earth metal carbonates, alkali metal bicarbonates and alkaline earth metal bicarbonates (such as sodium carbonate, potassium carbonate, sodium bicarbonate and calcium carbonate), calcium oxide, tertiary aliphatic and aromatic amines (such as triethylamine and N,N-dimethylaniline) and heterocyclic bases (such as pyridine and quinoline).

The reaction temperatures can be varied within a wide range. In general, the reaction is carried out at a temperature from −30° C. to +80° C., preferably between 0° C. and +40° C.

The reaction can be carried out under normal pressure and also at elevated pressure. It is carried out, in general, under normal pressure.

After the reaction of the compounds of formula (II) with the compounds of formula (III) has ended, the protective groups contained in the molecule are removed.

The cleavage of the sulphenyl protective groups can be effected with weak acids or with sulphur-containing, nucleophilic reagents, such as, for example, H$_2$S, thiophenol or 2-mercaptobenzthiazole, and the cleavage of the remaining protective groups can be effected with aqueous alkali metal hydroxide or alkaline earth metal hydroxide, or with acids such as trifluoroacetic acid, perchloric acid or boron trifluoride etherate.

If 3,2′,6′,3″-tetra-N-(o-nitrophenylsulphenyl)-sisomicin (the compound "(30)") and a compound "(6)" (as defined in Equation (a)) are used as starting materials, the course of the reaction can be represented by the following equation.

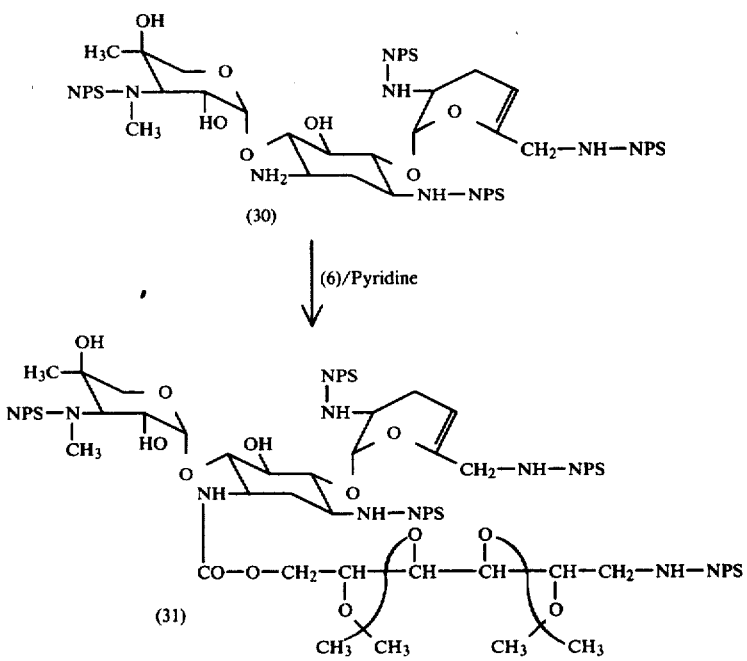

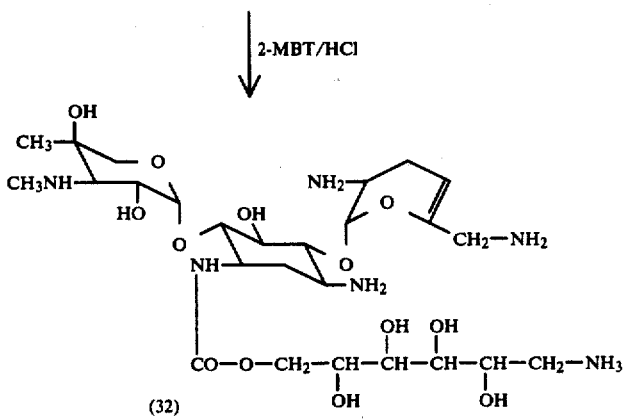

(32)

The following may be mentioned as examples of the active compounds according to the invention:

1-N-[(S,S)-, 1-N-[(R,R)-, 1-N-[(R,S)- and 1-N-[(S,R)-4-amino-2,3-dihydroxybutyloxycarbonyl]-sisomicin, 1-N-(3-amino-2,4-dihydroxybutyloxycarbonyl)-sisomicin, 1-N-(2-amino-3,4-dihydroxybutyloxycarbonyl)-sisomicin, 1-N-[(S,R)-, 1-N-[(R,S)-, 1-N-[(R,R)- and 1-N-[(S,S)-2,3,4-trihydroxybutyloxycarbonyl]-sisomicin, 1-N-(3-amino-1,4-dihydroxybut-2-yloxycarbonyl)-sisomicin, 1-N-(3-methylamino-1,4-dihydroxybut-2-yloxycarbonyl)-sisomicin, 1-N-(3-propylamino-1,4-dihydroxybut-2-yloxycarbonyl)-sisomicin, 1-N-(3-benzylamino-1,4-dihydroxybut-2-yloxycarbonyl)-sisomicin, 1-N-[3-(2-hydroxyethylamino)-1,4-dihydroxybut-2-yloxycarbonyl]-sisomicin, 1-N-[2-amino-2,2-bis-(hydroxymethyl)-ethyloxycarbonyl]-sisomicin, 1-N-[(S,S,R)-, 1-N-[(R,R,S)-, 1-N-[(R,S,R)-, 1-N-[(S,R,S)-, 1-N-[(S,R,R)-, 1-N-[(R,S,S)-, 1-N-[(R,R,R)- and 1-N[(S,S,S)-2,3,4,5-tetrahydroxypentyloxycarbonyl)]-sisomicin, 1-N-(5-amino-2,3,4-trihydroxypentyloxycarbonyl)-sisomicin, 1-N-[3-amino-2,2-bis-(hydroxymethyl)-propyloxycarbonyl]-sisomicin, 1-N-(2,3,4,5,6-pentahydroxyhexyloxycarbonyl)-sisomicin and 1-N-(6-amino-2,3,4,5-tetrahydroxyhexyloxycarbonyl)-sisomicin.

The compounds according to the invention are antimicrobial agents with a wide spectrum of action and with particular activity against gram-negative bacteria. These properties make it possible to use them as medicaments, particularly in combating the illnesses which are produced by bacteria and which occur in warm-blooded animals. They are particularly suitable for the prophylaxis and chemotherapy of local and systemic infections, particularly infections of the urogenital system, which are caused by gram-negative bacteria, for example *E. coli*, Proteus, Klebsiella and Pseudomonas, in medicine. Inhibitory areolae in the agar hole test were found, for example, against the following strains of bacteria in a concentration of 100 micrograms/1 ml:
Pseudomonas aerug. 5737,
Pseudomonas aerug. F 41,
Klebsiella pneum. 2 Munich,
Klebsiella pneum.
1 Düsseldorf,
E. coli Münster, and
E. coli Neumann.

As stated above, the invention also relates to the use in medicine of the compounds of the invention.

The present invention provides a pharmaceutical composition containing as active ingredient a compound of the invention in admixture with an inert pharmaceutical carrier, e.g. a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a composition of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, preferably humans, which comprises administering to the animals a compound of the invention alone or in admixture with a diluent or in the form of a medicament according to the invention. The dosage of the compounds according to the invention is usually similar to the dosage of the 1-N-unsubstituted compound. The dosage range in humans is generally from 0,3 mg to 30 mg per kg per day, preferably 1,5 to 7,5 mg per kg per day. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The compounds of the invention can be administered orally with the administration being effected in a single administration or distributed over several administrations and the compounds can also be administered topically.

In general, topical preparations contain approximately 0.1 to approximately 3.0 g of the compounds of the invention per 100 g of ointment, cream or lotion. The topical administration is effected approximately 2 to 5 times per day.

The pharmaceutical compositions according to the invention can occur in liquid form as solutions or suspensions for use in ears and eyes or for parenteral administration in the form of intramuscular or intravenous injections. Injection solutions or injection suspensions are usually administered so that approximately 1 to 15 mg of active compound per kilogram of body weight enter the infected organism in 2 to 4 doses per day.

For use in veterinary medicine the active compound can be mixed with animal feedstuffs. The present invention therefore also provides a medicated feed comprising the active compound of the present invention in admixture with a nutritious material.

The Examples which follow illustrate the preparation of the compounds according to the invention. If not otherwise indicated, data for quantities are to be understood as meaning parts by weight or percent by weight. Except as otherwise indicated, the compound numbers given in brackets in the Examples refer to the compounds previously indicated in the Equations (a) to (d) and the following formulae.

The following eluant systems were used for the chromatographic separations in the embodiment examples:

A. Toluene/ethyl acetate (2:1).
B. Methylene chloride/methanol (95:5).
C. Methylene chloride/methanol/20% aqueous ammonia (2:4:1).
D. Methylene chloride/methanol/17% aqueous ammonia (150:20:1).

The analytical separations were carried out over silica gel instant thin layer chromatography plates (Merck, Darmstadt), and the preparative separations using silica gel 60 (Merck, Darmstadt).

EXAMPLE 1

1-N-([S,S]-4-Amino-2,3-dihydroxy-butyloxycarbonyl)-sisomicin

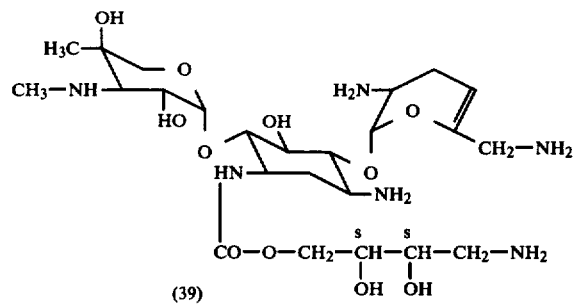

Equation:

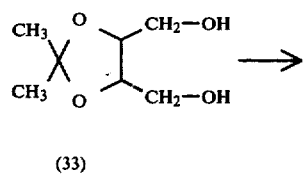

(33)

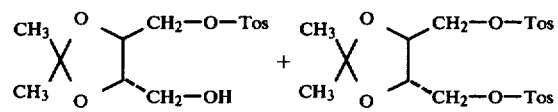

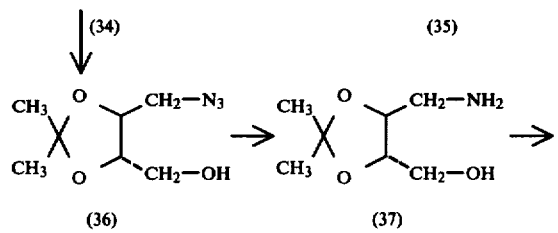

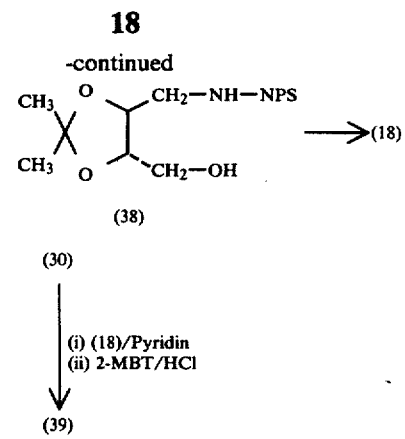

(a) Preparation of the compounds (34) and (35)

190.5 g of p-toluenesulphonic acid chloride (1 mol) were added in portions to a solution of 162 g (1 mol) of (+)-trans-4,5-bis[hydroxymethyl]-2,2-dimethyl-1,3-dioxolane (see Synthesis 1979, 350) in 600 ml of pyridine at −15° C., and the mixture was stirred until it was homogeneous. The mixture was kept at −25° overnight, concentrated in a high vacuum, stirred with system A, and filtered off from undissolved material. The mother liquor was subjected to chromatography over 1.4 kg of silica gel (system A) to separate the compounds (34) and (35).

Yield: Compound (34): 176 g of colourless oil (55.7%); Rf value (system A): 0.29; NMR: 1 tosyl radical Compound (35): 53 g of white crystals (11.3%); melting point 88°-91°; Rf value (system A): 0.78, NMR: 2 tosyl radicals.

(b) Preparation of compound (36)

A mixture of 162 g of compound (34) (0.51 mol) in 750 ml of dimethylformamide and 77 g of NaN₃ (1.18 mol) in 77 ml of water was heated under reflux for ½ a day and was concentrated in a high vacuum, stirred with a little of system A and filtered from the precipitate, and the mother liquor was filtered over 150 g of silica gel (eluant: system A).

Yield: 68.9 g (72%) of oil; IR: 2090/cm; Rf value (system A): 0.14.

(c) Preparation of compound (37)

63.9 g of compound (36) (0.34 mol) in 500 ml of ethyl acetate were hydrogenated during the course of 3 days using 4 g of Raney Ni, whilst hydrogen was passed through the mixture, and the reaction was monitored by means of thin layer chromatography (system A). The mixture was filtered off from the catalyst, and the filtrate was concentrated in vacuo.

Yield: 50 g (91%) of colourless oil; Rf value (system D): 0.29.

(d) Preparation of compound (38)

A solution of 59 g of 2-nitrophenylsulphenyl chloride (NPS-Cl) (0.21 mol)/300 ml of dioxan and 150 ml of 2 N NaOH were simultaneously added dropwise to a solution of 50 g of compound (37) (0.31 mol) in 300 ml of dioxan/156 ml of 2 N NaOH at pH>8, and the mixture was stirred for 2 hours at room temperature. The mixture was concentrated in vacuo, the residue was dissolved in 300 ml of methylene chloride, and 100 ml of water were added to the solution. The aqueous phase which had been separated off was extracted with twice 50 ml of methylene chloride, and the combined organic phases were washed with a total of 100 ml of water, dried with Na$_2$SO$_4$, concentrated in vacuo and filtered over 200 g of silica gel (eluant: system A).

Yield: 76 g (78%) of orange oil; Rf value (system A): 0.25.

(e) Preparation of compound (18)

48.8 g of p-nitrophenylchloroformate (0.24 mol) were added to a solution of 76 g of compound (38) (0.24 mol) in 450 ml of pyridine, and the mixture was stirred overnight at room temperature. When compound (38) could no longer be detected by means of thin layer chromatography, the mixture was concentrated in a high vacuum, and the residue was taken up in 200 ml of methylene chloride, washed with 3 times 75 ml of water and dried with Na$_2$SO$_4$. The solution was concentrated and was purified chromatographically (system A) over 300 g of silica gel. Yield: 81 g of orange oil; thin layer chromatography (system A): 1 principal component (Rf value 0.64), 1 minor component (Rf value 0.50) (identical with p-nitrophenol).

(f) Preparation of compound (39)

17.6 g of compound (18) (3.6×10$^{-2}$ mol) in 20 ml of methylene chloride were added to a solution of 33 g (3×10$^{-2}$ mol) of 3,2',6',3''-tetra-N-(o-nitrophenylsulphenyl)-sisomicin (compound (30)) (see German Published Specification No. 2,726,197) in 160 ml of pyridine, and the mixture was stirred for 1 day at room temperature. The mixture was concentrated in a high vacuum, and the intermediate product of the acylation was isolated by means of chromatography over 800 g of silica gel (system B; Rf value: 0.45): 39.5 g of an orange solid product (as a solidified foam). Cleavage of the NPS groups was effected by dissolving the product in 70 ml of methylene chloride, adding a solution of 85 g of 2-mercaptobenzthiazole in 300 ml of methanol/50 ml of methylene chloride, and acidifying the mixture with 15 ml of concentrated HCl. The mixture was extracted with twice 100 ml of water, the aqueous phase was washed with 3 times 50 ml of methylene chloride, and the acid aqueous solution was evaporated to 100 ml and was left to stand for 7 days at room temperature to split off the isopropylidene protective group. The solution was thereafter rendered alkaline with a commercial ion exchanger, and was concentrated and subjected to chromatography over 200 g of silica gel. The following fractions were isolated:

I. 3.5 g, thin layer chromatography (system C): 1 principal component (Rf value 0.13), 1 minor component (Rf value 0.24)=sisomicin.

II. 6.9 g, thin layer chromatography (system C): 1 principal product (Rf value 0.13), III 0.4 g, thin layer chromatography (system C): 1 principal product (Rf value 0.13), 1 trace (Rf value 0.08)

The fraction II contained the pure compound (39); in the fractions I and III, impurities were also present in addition to compound (39), the impurities being removed by a repeated chromatography.

EXAMPLE 2

1-N-([R,R]-4-Amino-2,3-dihydroxy-butyloxycarbonyl)-sisomicin

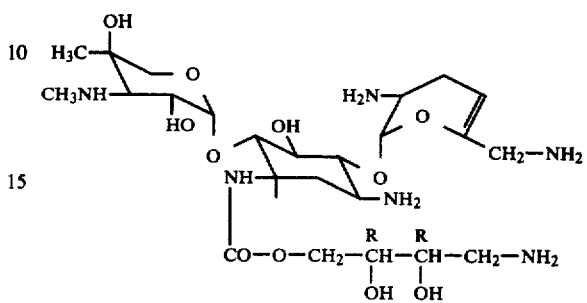

(4)

The preparation was effected analogously to Example 1, using (−)-trans-4,5-bis[hydroxymethyl]-2,2-dimethyl-1,3-dioxolan as the starting material, which was prepared from diethyl D(−)-tartrate, corresponding to compound (33), according to B. A. Murrer et al., Synthesis 1979, 350. The R$_f$ values of all the intermediate products were indentical with those of the corresponding isomers which are listed in Example 1. The $^{13}$C-NMR spectrum of compound (40) is recorded in Table 1:

TABLE 1

| $^{13}$C shifts δ (ppm, relative to TMS = 0) for (40) in D$_2$O | | |
|---|---|---|
| C atoms, i.e. assignment | Signal positions | Relative intensities |
| C-1'' | 100.441 | 3.772 |
| C-2'' | 70.962 | 3.052 |
| C-3'' | 64.239 | 3.193 |
| C-4'' | 72.824 | 3.795 |
| C-5'' | 69.390 | 2.429 |
| N—CH$_3$ at C-3'' | 37.456 | 3.689 |
| CH$_3$ at C-4'' | 22.388 | 4.200 |
| C-1 | 52.139 | 2.080 |
| C-2 | 32.225 | 2.101 |
| C-3 | 49.748 | 5.319 |
| C-4 | 81.618 | 1.736 |
| C-5 | 75.584 | 3.678 |
| C-6 | 84.105 | 2.072 |
| C-1' | 99.719 | 2.244 |
| C-2' | 47.229 | 4.758 |
| C-3' | 25.453 | 3.159 |
| C-4' | 98.836 | 3.621 |
| C-5' | 147.715 | 1.364 |
| C-6' | 43.362 | 2.885 |
| NH—CO—O— of the radical at 1-N | 158.483 | 1.308 |
| —OCH$_2$ of the radical at 1-N | 66.790 | 1.528 |
| —CH$_2$—NH$_2$ of the radical at 1-N | 42.752 | 4.055 |
| —CH(OH)—CH(OH)— of the radical at 1-N | 71.332 and 68.427 | 1.899 and 3.281 |

EXAMPLE 3

1-N-([R,S,R,S]-6-Amino-2,3,4,5-tetrahydroxy-hexyloxycarbonyl)-sisomicin

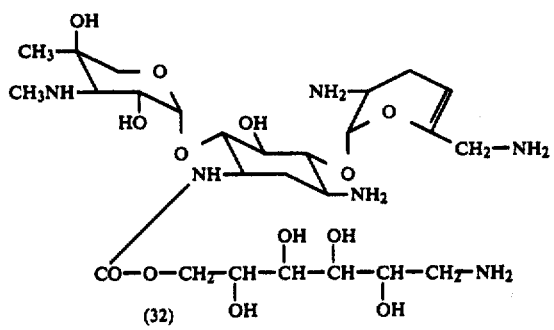

(32)

Equation (see Equation a)):

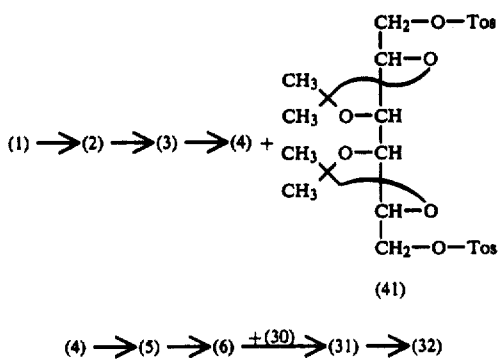

(4) → (5) → (6) → (30) → (31) → (32)

(a) Preparation of compound (2)

36 g of diethyl mucate (the compound (1)) (see J. Org. Chem. 18, 952 [1953]) were heated under reflux with 29.8 g of 2,2-dimethoxypropane (0.29 mol) and 0.3 g of p-toluenesulphonic acid in 400 ml of acetone for 13 hours, and the condensate was dried over 50 g of zeolite (4 Å; dried at 100° C./12 mm). For the working-up process, 0.2 g of $Na_2CO_3$ were added to the mixture, and it was filtered and concentrated, and the residue was recrystallised from 50 ml of ethanol.

Yield: 25.2 g (53%); melting point 85°-87° C.

IR: 1,760/cm; NMR ($CDCl_3$): δ=1.3 t (2 ester-$CH_3$), 1.47 d (6-isopropylidene-$CH_3$), 4.25 q (2 ester-$CH_2$), 4.5 m (4 OH). $R_f$ value (system A): 0.64

(b) Preparation of compound (3)

A suspension of 5.7 g of $LiAlH_4$ (0.15 mol) in 250 ml of absolute ether was initially introduced at 0° C. under $N_2$, and a solution of 24.3 g of compound (2) (0.07 mol) in 400 ml of absolute ether was added dropwise to the suspension at an internal temperature of 0°-15° C. during the course of 30 minutes. The suspension was then heated under reflux for 5 hours, and 15 ml of water and 15 ml of 4 N NaOH were carefully added to it at −10° C. to −5° C. under $N_2$. The precipitate was filtered off under suction, washed with ether and boiled for a further 3 hours with 250 ml of dioxan. The combined mother liquors were concentrated, and the residue was recrystallised from 25 ml of isopropanol.

Yield: 6.3 g (29.4%), melting point 111°-113° C.; $R_f$ value (system A): 0.1. NMR ($CDCl_3$): δ=1.4 broad s (4 isopropylidene-$CH_3$), 2.62 s (2 OH; exchange with $CD_3OD$), 3.82 m (2 $CH_2$-O), 4.0 m (4 CH-O).

(c) Preparation of compounds (4) and (41)

6 g of compound (3) (0.023 mol) were dissolved in 15 ml of absolute pyridine, and 4.4 g of p-toluenesulphonic acid chloride (0.023 mol) were added in portions to the solution at −15° C. during the course of 5 minutes. The mixture was further stirred at −15° C. until it was homogeneous, and was left to stand overnight at −25° C. to −30° C. and stirred with 100 ml of water at 0° C. The precipitate which separated out was filtered off under suction, washed with water and dried at 40° C./12 mm (7.5 g). To separate the two components, the mixture was subjected to chromatography over 150 g of silica gel, using $CH_2Cl_2$/methanol (99:1) as the eluant:

Compound (41): 2 g, melting point 164°-166° C.; $R_f$ value 0.72; NMR shows 2 tosyl radicals.

Compound (4): 3.5 g, melting point 83°-84° C.; $R_f$ value 0.29; NMR shows 1 tosyl radical.

(d) Preparation of compound (5)

A solution of 1.2 g of $NaN_3$ ($1.84 \times 10^{-2}$ mol) in 2 ml of water were added to 3.33 g of compound (4) ($8.3 \times 10^{-3}$ mol) in 15 ml of dimethylformamide, and the mixture was heated under reflux for 9 hours. The mixture was concentrated in vacuo, the residue was stirred with a little toluene/ethyl acetate (2:1), the solution was filtered off from the salt, and the filtrate was subjected to chromatography over 150 g of silica gel using system A as the eluant.

Yield: 1.5 g of oil (62.2%); IR: 2,100/cm; $R_f$ value (system A): 0.27.

1.5 g ($5.2 \times 10^{-3}$ mol) of the oil thus obtained were hydrogenated at room temperature and under normal pressure in 80 ml of ethyl acetate, using 1 g of Pt black, for 2 days, and the reaction was monitored by thin layer chromatography. The catalyst was filtered off, the filtrate was concentrated, and a white solid product was obtained, which, according to thin layer chromatography (system A), no longer contained azide.

Yield: 1.1 g (81%), melting point 130°-133° C.

(e) Preparation of compound (6)

0.91 g of compound (5) ($3 \times 10^{-3}$ mol) were initially introduced into 3.5 ml of dioxan and 1.75 ml of 2 N NaOH, and a solution of 0.65 g of NPS-Cl ($3.5 \times 10^{-3}$ mol) in 3.5 ml of dioxan and 2.2 ml of 2 N NaOH were silultaneously added dropwise at pH 8-9. After 60 minutes, a new component could be detected in the thin layer chromatography (system A), and the component was obtained in pure form after evaporating the solvent by filtration over 30 g of silica gel with system A.

Yield: 0.8 g (64%), melting point 112°-115° C.; $R_f$ value (system A): 0.2

NMR ($CDCl_3$):=1.38 2 d (4 isopropylidene-$CH_3$), 2.22 t broad (OH), 3.23 m (3H), 3.78 m (6H), 7.0-8.4 m (4H, NPS radical).

A solution of 750 mg ($1.8 \times 10^{-3}$ mol) of the product, which was obtained in this manner, in 4 ml of absolute pyridine was stirred for 2 hours at room temperature with 360 mg of p-nitrophenyl chloroformate ($1.8 \times 10^{-3}$ mol), and the mixture was then concentrated in a high vacuum and was purified chromatographically over 30 g of silica gel using system A.

Yield: 0.9 g; $R_f$ value (system A): 0.54.

(f) Preparation of compound (32)

260 mg of compound (6) were added to a solution of 330 mg of 3,2',6',3''''-tetra-N-(o-nitrophenylsulphenyl)-sisomicin (30) ($3 \times 10^{-4}$ mol) in 1.5 ml of pyridine, and the mixture was left to stand overnight at room temperature. After the solution had been concentrated by evaporation, the reaction product (compound (31)) was isolated over 40 g of silica gel (system B) and was cleaved analogously to Example (1 f). To split off the two isopropylidene groups, the acid aqueous solution remained standing for 11 days at room temperature, the stepwise cleavage taking place very slowly via a monoisopropylidene derivative ($R_f$ value: 0.34; system C) to give the completely de-blocked derivative ($R_f$ value: 0.02; system C). The mixture was then rendered alkaline with a commercial ion exchanger, was concentrated, and was purified by subjecting it to chromatography over 5 g of silica gel using system C as the eluant.

Yield: 47 mg (24%)

$R_f$ value (system C): 0.02 (for comparison: sisomicin $R_f$=0.16)

The $^{13}$C spectrum of (32) is recorded in Table 2:

TABLE 2

| C atoms, i.e. assignment | $^{13}$C shifts δ (ppm, relative to TMS = 0) for (32) in D$_2$O | |
|---|---|---|
| | Signal positions | Relative intensities |
| C-1" | 101.271 | <1 |
| C-2" | 70.272 | 2.262 |
| C-3" | 64.463 (see below) | 3.330 |
| C-4" | 72.487 | 3.097 |
| C-5" | 68.957 | 2.959 |
| N—CH$_3$ at C-3" | 37.135 | 4.049 |
| CH$_3$ at C-4" | 22.308 | 4.699 |

TABLE 2-continued

| C atoms, i.e. assignment | $^{13}$C shifts δ (ppm, relative to TMS = 0) for (32) in D$_2$O | |
|---|---|---|
| | Signal positions | Relative intensities |
| C-1 | 52.139 | 2.090 |
| C-2 | 35.586 | 2.492 |
| C-3 | 49.764 | 7.372 |
| C-4 | 81.651 | <1 |
| C-5 | 75.584 | 2.961 |
| C-6 | 83.688 | 1.863 |
| C-1' | 100.136 | 4.549 |
| C-2' | 47.133 | 4.413 |
| C-3' | 25.453 | 3.222 |
| C-4' | 99.590 | 2.792 |
| C-5' | 145.946 | <1(broad) |
| C-6' | 43.891 | 3.669 |
| CO of the radical at N-1 | 158.579 | 1.907 |
| CH$_2$NH$_2$ of the radical at N-1 | 42.415 | 4.160 |
| CHOH, α to CH$_2$ of the radical at N-1 | 71.127 | 3.092 |
| residual CHOH of the radical | 68.3 | 4.936 (broadened) |
| CH$_2$O of the radical at N-1 | 64.46 (see above) | 3.330 |

EXAMPLE 4

1-N-(3-Amino-2,2-bis-[hydroxymethyl]-propyloxycarbonyl)-sisomicin (51)

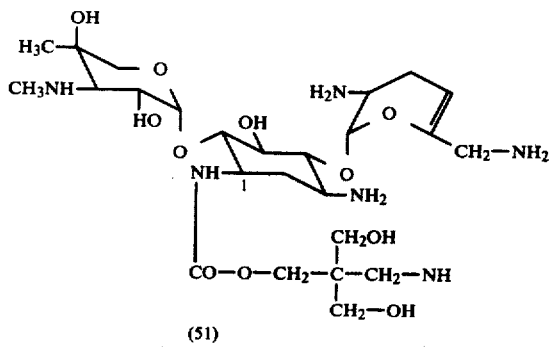

(51)

Equation:

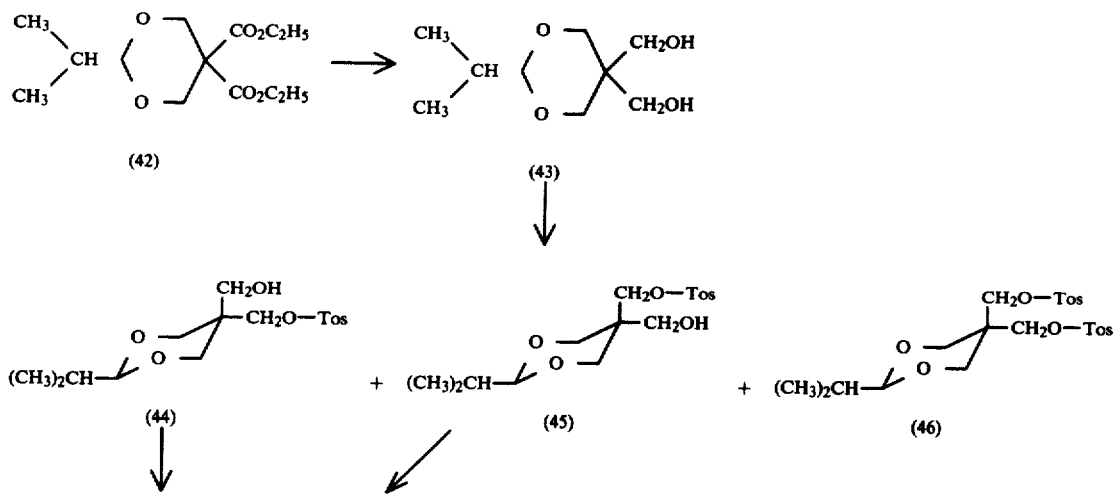

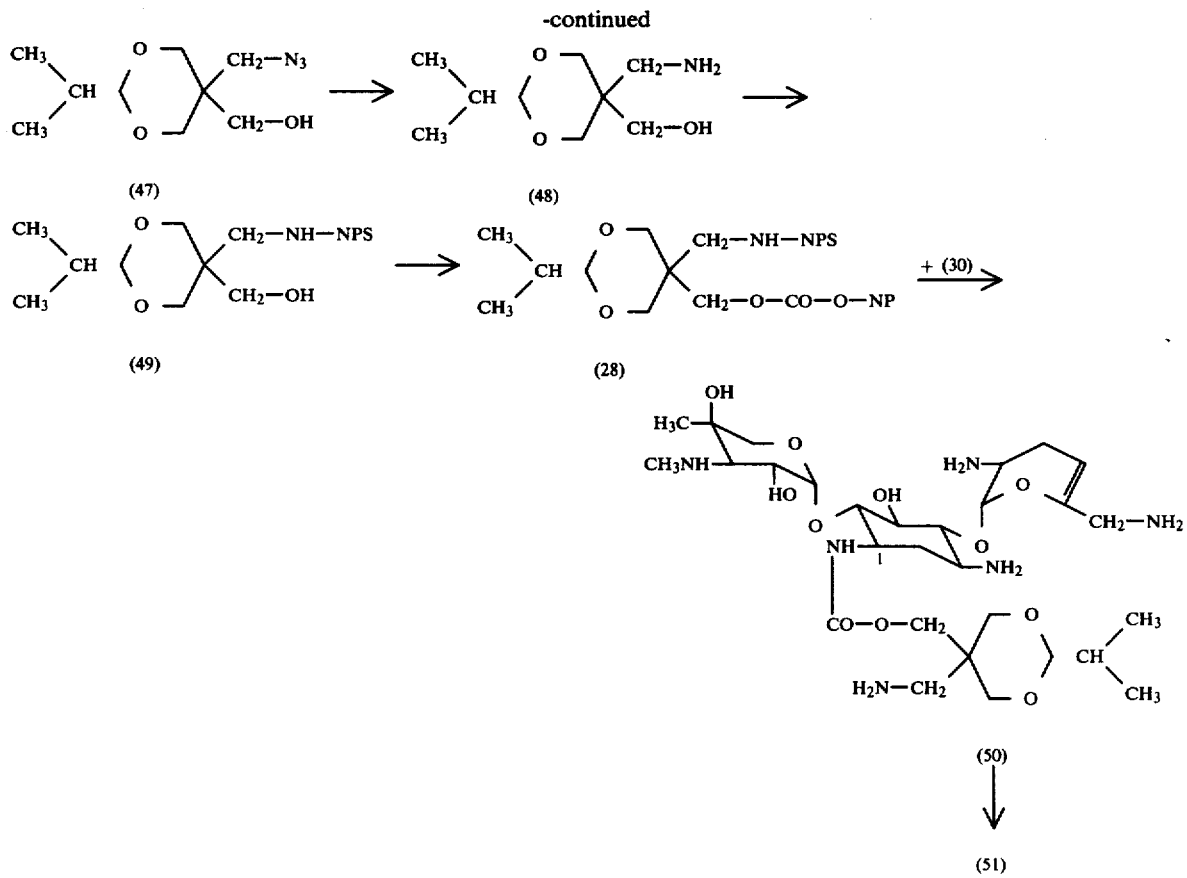

(a) Preparation of compound (43)

A solution of 55.5 g of compound (42) (see J. Amer. Chem. Soc. 94, 171 [1972]) (0.20 mol) in 150 ml of ether was added dropwise to a suspension of 16.9 g of LiAlH$_4$ (0.45 mol) in 150 ml of ether during the course of 90 minutes, and the mixture was heated under reflux for 5 hours. 20 ml of water were carefully added to the mixture at $-5°$ C., the latter was diluted with 250 ml of ether and was filtered, and the residue was rinsed with ether. The precipitate was boiled with 300 ml of dioxan for 3 hours, and the combined organic phases were dried with Na$_2$SO$_4$, filtered and concentrated. The solid residue was recrystallised from 20 ml of isopropanol.

Yield: 4.6 g (12.5%), melting point 99°–100° C. NMR: A mixture of the two conformers.

(b) Preparation of compounds (44), (45) and (46)

5 g of p-toluenesulphonic acid chloride (0.025 mol) were added in portions to 4 g of compound (43) (0.02 mol) in 12 ml of absolute pyridine at $-15°$ C., and the mixture was stirred until it was homogeneous. The mixture was left to stand overnight at 25° C., and was concentrated in vacuo and subjected to chromatography over 100 g of silica gel with system A.

Compound (46): 0.4 g of oil; R$_f$ value (system A): 0.84
Compound (44): 0.9 g white crystals; melting point 103°–106° C.; R$_f$ value (system A): 0.5
Compound (45): 1.0 g of white crystals; melting point 73°–75° C.; R$_f$ value (system A): 0.4

(c) Preparation of compound (47)

390 mg of NaN$_3$ in 0.5 ml of water were added to 0.9 g of the product of Example (4b) (2.6×10$^{-3}$ mol) in 3 ml of dimethylformamide, and the mixture was heated under reflux for 5 hours, concentrated and filtered over 50 g of silica gel (eluant: system A).

Yield: 0.5 g of oil (89%); IR: 2,100/cm; R$_f$ value (system A): 0.57.

(d) Preparation of compound (48)

0.5 g of compound (47) (2.3×10$^{-3}$ mol) were hydrogenated in an H$_2$ stream in 20 ml of ethyl acetate, using 0.3 g of Pt black, during the course of 6 days, and the reduction in quantity of the starting compound was monitored by means of thin layer chromatography (system A). After the catalyst had been filtered off, the mixture was concentrated in vacuo.

Yield: 0.3 g (69%).

(e) Preparation of compound (49)

0.3 g of o-nitrophenylsulphenyl chloride (1.5×10$^{-3}$ mol) in 1.5 ml of dioxan and 0.9 ml of 2 N NaOH were added simultaneously to 0.3 g of compound (48) (1.58×10$^{-3}$ mol) in 1.5 ml of dioxan and 0.75 ml of 2 N NaOH at pH >8. After 15 hours, the mixture was concentrated in vacuo, taken up in 5 ml of CH$_2$Cl$_2$, washed with twice 3 ml of water, dried with Na$_2$SO$_4$, concentrated and purified over 50 g of silica gel (eluant: system A).

Yield: 0.4 g (74%); R$_f$ value (system A): 0.42.

(f) Preparation of compound (28)

A solution of 0.4 g of (49) (1.1×10$^{-3}$ mol) in 2 ml of pyridine was stirred with 0.22 g of p-nitrophenyl chloroformate (1.1×10$^{-3}$ mol) for 5 hours at room temperature, and the mixture was concentrated in a high vacuum and was subjected to chromatography over 50 g of silica gel with system A.

Yield: 0.3 g (54%); IR: 1,770/cm; R$_f$ value (system A): 0.7.

(g) Preparation of compounds (50) and (51)

91 mg of compound (28) ($1.8 \times 10^{-4}$ mol) were added to 165 mg of 3,2',6',3''-tetra-N-(o-nitrophenylsulphenyl)-sisomicin (the compound (30)) ($1.5 \times 10^{-4}$ mol) in 0.75 ml of pyridine, and the mixture was left to stand overnight at room temperature and was concentrated in a high vacuum. The reaction product was separated off over 20 g of silica gel using system B, was taken up in 0.9 ml of $CH_2Cl_2$, and, to split off the o-nitrophenylsulphenyl protective groups, a solution of 255 mg of 2-mercaptobenzthiazole ($1.5 \times 10^{-3}$ mol) in 0.9 ml of methanol/1.5 ml of methylene chloride and a little concentrated hydrochloric acid were added, the latter until an acid reaction was obtained, and the mixture was diluted with 1 ml of water. The acid solution remained standing for 2 days at room temperature, it being intended that the isobutylidene group be removed from the primary cleavage product. Since, according to thin layer chromatography, the first cleavage product was still present in an unchanged form after this period, it was isolated, for a structure determination, by the addition of an ion exchanger in the (OH—) form, concentration and chromatography over 5 g of silica gel (system C).

Yield: 43 mg of a colourless solid product; $R_f$ value (system C): 0.62 (sisomicin: $R_f$ value: 0.24).

The $^{13}$C-NMR (see Table 3) showed the presence of the structure of compound (50), and therefore of the isobutylidene group. Its cleavage was effected by again taking up the compound in 1.2 ml of 6.5% strength hydrochloric acid and leaving the mixture to stand for 2 days at room temperature. The mixture was rendered alkaline with an ion exchanger in the (OH—) form, and was thereafter concentrated and subjected to chromatography over 5 g of silica gel (system C), compound (51) being obtained in pure form:

Yield: 10 mg; $R_f$ value (system C): 0.23 (Sisomicin: $R_f$ value: 0.24).

TABLE 3

| $^{13}$C shifts δ (ppm, relative to TMS = 0) for (50) in $D_2O$ | | |
|---|---|---|
| C atoms, i.e. assignment | Signal positions | Relative intensities |
| C-1'' | 100.665 | 3.916 |
| C-2'' | 70.786 | 4.153 |
| C-3'' | 70.609 | 2.401 |
| C-4'' | 73.049 | 5.285 |
| C-5'' | 68.571 | 3.577 |
| N—CH$_3$ at C-3'' | 7.665 | 4.329 |
| CH$_3$ at C-4'' | 22.533 | 3.108 |
| C-1 | 52.027 | 1.978 |
| C-2 | 32.546 | 5.679 |
| C-3 | 49.845 | 4.094 |
| C-4 | 81.818 | 1.801 |
| C-5 | 75.552 | 3.809 |
| C-6 | 84.442 | 2.779 |
| C-1' | 99.719 | 3.072 |
| C-2' | 47.341 | 4.233 |
| C-3' | 25.485 | 2.715 |
| C-4' | 97.665 | 4.341 |
| C-5' | 149.208 | 2.514 |
| C-6' | 43.105 | 4.841 |
| (CH$_3$)$_2$ of the radical at N-1 | 16.788 | 8.721 |
| NH—COO of the radical at N-1 | 158.675 | 2.167 |
| C-2 of the radical at N-1 | 106.908 | 4.671 |
| C-4/C-6 of the radical at N-1 | 64.255 | 4.215 |
| OCH$_2$ at C-5 of the radical at N-1 | 69.631 | 2.422 |
| CH$_2$NH$_2$ at C-5 of the radical at N-1 | 42.575 | 3.055 |
| C-5 of the radical at N-1 | 38.210 | 5.400 |
| CH of isopropyl of the radical at N-1 | 35.611 | 2.061 |

EXAMPLE 5

1-N-(2-Amino-3-hydroxy-2-hydroxymethyl-propyloxycarbonyl)sisomicin

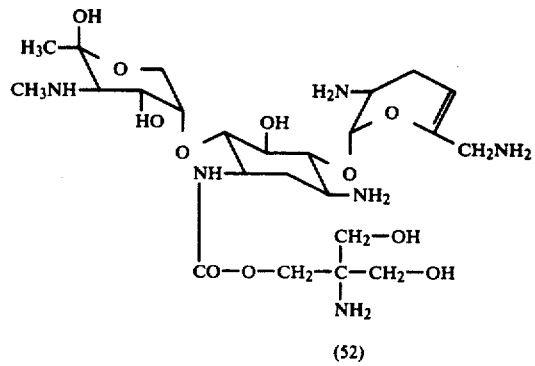

(52)

Equation:

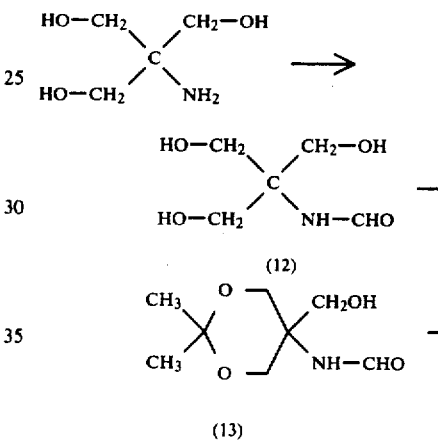

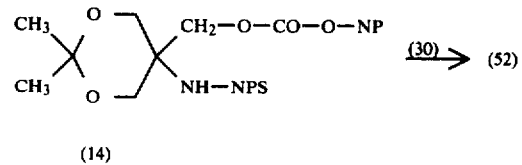

(a) Preparation of compound (12)

60.5 g (0.5 mol) of 2-amino-2-hydroxymethyl-1,3-propanediol were heated under reflux in 200 ml of methanol with 42 g of methyl formate (0.7 mol) for 4 hours. The crystals which were precipitated on cooling the mixture were filtered off under suction and washed with methanol.

Yield: 60.8 g (91.4%), melting point 117°–118° C., IR: 1,670, 1,645/cm.

NMR (d$_6$-DMSO): δ = ~3.5 2 signals (3CH$_2$), 4.83 s broad (3OH), 6.83 d and 7.52 s broad (NH), 8.0 d and 8.2 d (CHO).

(b) Preparation of compound (13)

29.8 g of compound (12) (0.2 mol) were heated under reflux in 150 ml of dimethylformamide with 200 ml of 2,2-dimetoxypropane and 200 mg of p-toluenesulphonic acid for 4 hours, the mixture was cooled and was poured into 1 liter of 0.5% NaHCO$_3$ solution, and the latter was extracted with 3 times 150 ml of methylene chloride. The solution which had been dried with Na$_2$SO$_4$ was concentrated, and the residual red-brown oil (3 g) was subjected to chromatography over 100 g of silica gel using system D.

Yield: 2.2 g (5.5%); $R_f$ value (system D): 0.8; IR: 1,670/cm.

(c) Preparation of compound (14)

3.8 g of compound (13) (0.02 mol) were heated under reflux with a solution of 10 g of Ba(OH)$_2$. 8H$_2$O in 50 ml of water for 5 hours, the mixture was concentrated, and the residue was stirred with 5 ml of system D. The undissolved salts were filtered off, and the filtrate was subjected to chromatography over 100 g of silica gel (system D):

Yield: 0.4 g (12.4%), $R_f$ value (system D): 0.32.

300 mg (1.8 × 10$^{-3}$ mol) of the amine thus obtained were acylated at room temperature in 2 ml of dioxan/1 ml of 2 N NaOH by the simultaneous dropwise addition of 355 mg of NPS-Cl (1.8 × 10$^{-3}$ mol) in 2 ml of dioxan and 1.3 ml of 2 N NaOH. The product was worked up by concentration, dissolving in methylene chloride, washing with water, drying with Na$_2$SO$_4$ and chromatography (system A) over 40 g of silica gel.

Yield: 0.2 g of a yellow solid product (35%), Melting point 148°–150° C.; $R_f$ value (system A): 0.15.

0.2 g (6.4 × 10$^{-4}$ mol) of the acylated product thus obtained was reacted in 1.5 ml of pyridine with 188 mg of p-nitrophenyl chloroformate at room temperature for 4 hours. The mixture was concentrated, was taken up in 5 ml of methylene chloride, extracted with twice 1.5 ml of water and dried with Na$_2$SO$_4$. The product (compound (14)) isolated after chromatography over 40 g of silica gel (system A) also contained, in addition to the principal component ($R_f$ value 0.48), nitrophenol and a further impurity ($R_f$ value 0.68), and could be directly used for further reaction.

IR: 1,760 cm$^{-1}$.

(d) Preparation of the compound (52)

165 mg of 3,2′,6′,3″-tetra-N-(o-nitrophenylsulphenyl)-sisomicin (compound (30)) (1.5 × 10$^{-4}$ mol) were dissolved in 0.75 ml of pyridine, 90 mg of compound (14) were added to the solution, and the latter was stirred for 1 day at room temperature. The working-up was effected analogously to Example (1f), the end product being purified chromatographically over 5 g of silica gel (system C).

Yield: 21 mg (23.6%); $R_f$ value (system C): 0.34 (sisomicin: $R_f$ value: 0.25).

EXAMPLE 6

1-N-(1,4-Dihydroxy-3-n-propylamino-but-2-yloxycarbonyl)-sisomicin (a compound (53a))

Equation:

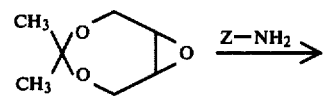 

(8)

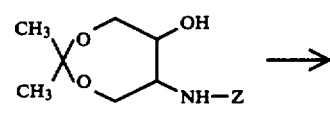 

(9)

Equation:

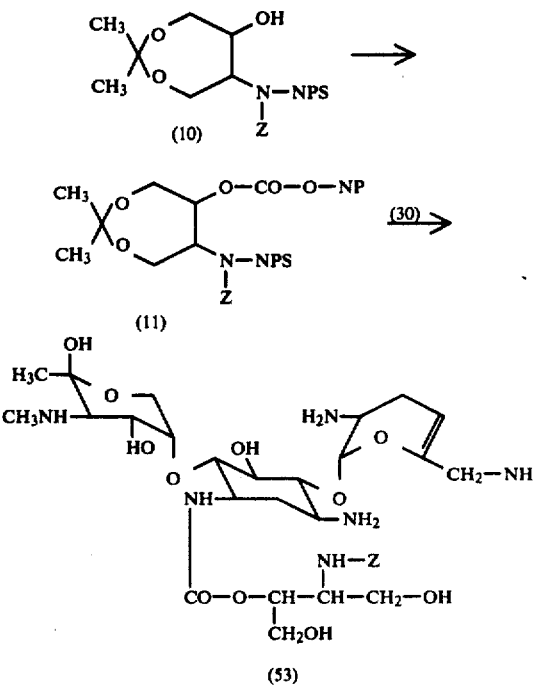

a: Z = C$_3$H$_7$
b: Z = H
c: Z = n-C$_4$H$_9$
d: Z = CH$_2$CH$_2$—O—C(C$_6$H$_5$)$_3$
e: Z = CH$_2$CH$_2$—OH (a) Preparation of compound (9a) (with Z=n—C$_3$H$_7$)

5.76 g (0.04 mol) of 4,4-dimethyl-3,5,8-trioxabicyclo[5.1.0]octane (compound (8)) (see J. Org. Chem. 41, 2469 [1976]) were heated under reflux in 20 ml of methylene chloride with 2.4 g of n-propylamine for 10 hours, and the mixture was then concentrated in vacuo at 40° C.

Yield: 7.3 g of oil (90%); $R_f$ value (system D): 0.33.

(b) Preparation of compound (10a)

A solution of 0.95 g of NPS-Cl in 2.5 ml of dioxan and 2.5 ml of 2 N NaOH were added simultaneously to a solution of 1 g of compound (9a) (0.005 mol) in 7 ml of dioxan at pH>8. The mixture was stirred for a few hours at room temperature, and was concentrated in vacuo, taken up in methylene chloride, washed with water, dried with Na$_2$SO$_4$ and concentrated by evaporation. It was purified by chromatography over 60 g of silica gel, using toluene as the eluant.

Yield: 1 g of orange oil, Rf value (system A): 0.4

(c) Preparation of compound (11a)

0.89 of compound (10a) (0.0025 mol) were reacted in 7.5 ml of pyridine with 0.5 g of p-nitrophenyl chloroformate, and the reaction mixture was worked up analogously to Example (1e).

Yield: 1.1 g (84%); Rf value (system A): 0.76; IR: 1,770/cm.

(d) Preparation of compound (53a)

A solution of 165 mg (1.5 × 10$^{-4}$ mol) of 3,2′,6′,3″-tetra-N-(o-nitrophenylsulphenyl)-sisomicin (30) in 0.75 ml of pyridine were reacted with 90 mg of compound (11a), and the reaction mixture was worked up according to Example (1f). The cleavage of the isopropylidene protective group was quantitative after the acid aqueous solution had been standing for 2 hours.

Yield: 20 mg (21%); Rf value (system C): 0.51 (sisomicin: 0.24).

EXAMPLE 7

1-N-(1,4-Dihydroxy-3-amino-but-2-yloxycarbonyl)-sisomicin (a compound (53b))

The preparation was effected according to Example 6, using NH3, via the stages of compounds (9b) (Rf value [system D]=0.20), (10b) (Rf value [system A]: 0.20) and (11b) (Rf value [system A]=0.68; IR=1,780/cm) in a yield of 18%. Rf value (system C): 0.27 (sisomicin: 0.25).

EXAMPLE 8

1-N-(1,4-Dihydroxy-3-n-butylamino-but-2-yloxycarbonyl)-sisomicin (a compound (53c))

The preparation was effected according to Example 6, using n-butylamine, via the stages of compounds (9c) (Rf value [system D]: 0.57; melting point 156°), (10c) (Rf value [system A]: 0.37) and (11c) (IR: 1,780/cm), in a yield of 30%; Rf value (system C): 0.54.

EXAMPLE 9

1-N-[1,4-Dihydroxy-3-(2-hydroxyethylamino)-but-2-yloxycarbonyl]-sisomicin (a compound (53e))

The preparation was effected according to Example 6, using O-tritylethanolamine, via the stages of compounds (9d) (Rf value [system D]: 0.7), (10d) (Rf value [system A]: 0.42) and (11d) (Rf value [system A]: 0.92), to give the compound (53d), the O-trityl protective group being split off in the last step, with the formation of the compound (53e), by leaving the acid aqueous solution to stand for 15 hours.

Yield: 49%, Rf value (system C): 0.38.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the patient's body to the active compound.

What is claimed is:

1. A compound, which is 1-N-([R,S,R,S]-6-Amino-2,3,4,5-tetrahydroxy-hexyloxy-carbonyl)-sisomicin or a salt thereof.

2. A compound, which is 1-N-(3-Amino-2,2-bis-[hydroxymethyl]-propyloxycarbonyl)-sisomicin or a salt thereof.

* * * * *